(12) United States Patent
Vedoy

(10) Patent No.: US 11,387,498 B2
(45) Date of Patent: Jul. 12, 2022

(54) BATTERY LITHIUM CLUSTER GROWTH CONTROL

(71) Applicant: Cardiac Pacemakers, Inc., St. Paul, MN (US)

(72) Inventor: Arild Vedoy, Forest Lake, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

(21) Appl. No.: 17/181,355

(22) Filed: Feb. 22, 2021

(65) Prior Publication Data

US 2021/0184318 A1 Jun. 17, 2021

Related U.S. Application Data

(63) Continuation of application No. 16/847,823, filed on Apr. 14, 2020, now Pat. No. 10,957,890, which is a
(Continued)

(51) Int. Cl.
| | | |
|---|---|---|
| *H01M 10/42* | (2006.01) | |
| *H01M 10/04* | (2006.01) | |
| *H01M 50/502* | (2021.01) | |
| *H01M 50/103* | (2021.01) | |
| *H01M 50/172* | (2021.01) | |

(Continued)

(52) U.S. Cl.
CPC ........ *H01M 10/4235* (2013.01); *A61N 1/378* (2013.01); *H01M 4/134* (2013.01); *H01M 4/382* (2013.01); *H01M 10/0436* (2013.01); *H01M 10/0459* (2013.01); *H01M 10/0525* (2013.01); *H01M 50/103* (2021.01); *H01M 50/172* (2021.01); *H01M 50/463* (2021.01);

*H01M 50/489* (2021.01); *H01M 50/502* (2021.01); *H01M 50/543* (2021.01); *H01M 50/668* (2021.01); *H01M 10/052* (2013.01);
(Continued)

(58) Field of Classification Search
CPC ......... H01M 10/0459; H01M 10/0435; H01M 50/489; H01M 50/668
USPC ....................................................... 429/153
See application file for complete search history.

(56) References Cited

U.S. PATENT DOCUMENTS

| | | |
|---|---|---|
| 6,040,082 A | 3/2000 | Haas et al. |
| 6,229,760 B1 | 5/2001 | Ambs |

(Continued)

FOREIGN PATENT DOCUMENTS

| | | |
|---|---|---|
| CN | 109075374 A | 12/2018 |
| JP | 2004501729 A | 1/2004 |

(Continued)

OTHER PUBLICATIONS

"U.S. Appl. No. 15/583,660, Advisory Action dated Aug. 22, 2019", 3 pgs.
(Continued)

*Primary Examiner* — James M Erwin
(74) *Attorney, Agent, or Firm* — Schwegman Lundberg & Woessner, P.A.

(57) ABSTRACT

An apparatus includes a battery stack including a plurality of alternating anodes and cathodes, wherein each of the anodes is positioned between first and second separators, and wherein a tab of the anode extends out from between the first and second separators, and an edge tape extending across a top of the first and second separators.

20 Claims, 5 Drawing Sheets

Related U.S. Application Data continuation of application No. 15/583,660, filed on May 1, 2017, now Pat. No. 10,665,845.

(60) Provisional application No. 62/330,317, filed on May 2, 2016.

(51) Int. Cl.

| | |
|---|---|
| *H01M 50/463* | (2021.01) |
| *H01M 50/543* | (2021.01) |
| *H01M 50/60* | (2021.01) |
| *H01M 50/489* | (2021.01) |
| *A61N 1/378* | (2006.01) |
| *H01M 4/134* | (2010.01) |
| *H01M 4/38* | (2006.01) |
| *H01M 10/0525* | (2010.01) |
| *H01M 10/052* | (2010.01) |
| *H01M 10/0585* | (2010.01) |
| *H01M 4/02* | (2006.01) |

(52) U.S. Cl.
CPC .. *H01M 10/0585* (2013.01); *H01M 2004/027* (2013.01); *H01M 2220/30* (2013.01)

(56) References Cited

U.S. PATENT DOCUMENTS

| | | | |
|---|---|---|---|
| 6,229,772 B1 | 5/2001 | Kumagai | |
| 6,245,464 B1 | 6/2001 | Spillman et al. | |
| 6,541,497 B1 | 4/2003 | Dominianni et al. | |
| 6,541,711 B1 | 4/2003 | Dube et al. | |
| 6,552,696 B1 | 4/2003 | Sievenpioer et al. | |
| 6,552,700 B2 | 4/2003 | Narui | |
| 6,552,709 B1 | 4/2003 | Yamaguchi | |
| 6,678,559 B1 | 1/2004 | Breyen et al. | |
| 6,881,516 B2 | 4/2005 | Aamodt et al. | |
| 7,901,808 B2 | 3/2011 | Morgan et al. | |
| 7,968,226 B2 | 6/2011 | Aamodt et al. | |
| 8,389,155 B2 | 3/2013 | Aamondt et al. | |
| 8,557,431 B2 | 10/2013 | Park et al. | |
| 8,916,290 B2 | 12/2014 | Aamodt et al. | |
| 8,974,949 B2 | 3/2015 | Kuhn et al. | |
| 9,011,709 B2 | 4/2015 | Choi | |
| 2004/0127952 A1 | 7/2004 | O'Phelan et al. | |
| 2006/0012943 A1 | 1/2006 | Sherwood | |
| 2009/0259265 A1 | 10/2009 | Stevenson et al. | |
| 2011/0151332 A1 | 6/2011 | Morgan et al. | |
| 2012/0121989 A1* | 5/2012 | Roberts | H01M 4/366 429/342 |
| 2014/0272527 A1* | 9/2014 | Venkatesan | H01M 50/411 29/623.5 |
| 2015/0147626 A1 | 5/2015 | Tajima et al. | |
| 2017/0317331 A1 | 11/2017 | Vedoy | |
| 2020/0243829 A1 | 7/2020 | Vedoy | |

FOREIGN PATENT DOCUMENTS

| | | |
|---|---|---|
| JP | 2015128057 A | 7/2015 |
| JP | 2019514580 A | 6/2019 |
| WO | WO-2017192455 A1 | 11/2017 |

OTHER PUBLICATIONS

"U.S. Appl. No. 15/583,660, Final Office Action dated Jun. 13, 2019", 13 pgs.

"U.S. Appl. No. 15/583,660, Non Final Office Action dated Jan. 7, 2019", 12 pgs.

"U.S. Appl. No. 15/583,660, Non Final Office Action dated Sep. 25, 2019", 14 pgs.

"U.S. Appl. No. 15/583,660, Notice of Allowance dated Jan. 14, 2020", 8 pgs.

"U.S. Appl. No. 15/583,660, Response filed Dec. 23, 2019 to Non Final Office Action dated Sep. 25, 2019", 9 pgs.

"U.S. Appl. No. 15/583,660, Response filed Aug. 13, 2019 to Final Office Action dated Jun. 13, 2019", 9 pgs.

"U.S. Appl. No. 15/583,660, Response to Non Final Office Action Apr. 8, 2019", 9 pgs.

"U.S. Appl. No. 16/847,823, Notice of Allowance dated Nov. 17, 2020", 8 pgs.

"Australian Application Serial No. 2017261222, First Examination Report dated Jun. 4, 2019", 4 pgs.

"Australian Application Serial No. 2017261222, Response filed Jan. 13, 2020 to First Examination Report dated Jun. 4, 2019", 15 pgs.

"Australian Application Serial No. 2017261222, Response filed Mar. 9, 2020 to Second Examiners Report dated Feb. 6, 2020", 2 pgs.

"Australian Application Serial No. 2017261222, Second Examiners Report dated Feb. 6, 2020", 4 pgs.

"European Application Serial No. 17732630.3, Communication Pursuant to Article 94(3) EPC dated Feb. 11, 2020", 4 pgs.

"European Application Serial No. 17732630.3, Response Filed Jun. 21, 2019 to Communication pursuant to Rules 161(2) and 162 EPC dated Dec. 21, 2018", 15 pgs.

"International Application Serial No. PCT/US2017/030422, International Preliminary Report on Patentability dated Nov. 15, 2018", 9 pgs.

"International Application Serial No. PCT/US2017/030422, International Search Report dated Aug. 9, 2017", 4 pgs.

"International Application Serial No. PCT/US2017/030422, Written Opinion dated Aug. 9, 2017", 7 pgs.

"Japanese Application Serial No. 2018-557425, Notification of Reasons for Refusal dated Oct. 1, 2019", W/ English Translation, 8 pgs.

"Japanese Application Serial No. 2018-557425, Response filed Jan. 6, 2020 to Notification of Reasons for Refusal dated Oct. 1, 2019", w/ English claims, 7 pgs.

* cited by examiner

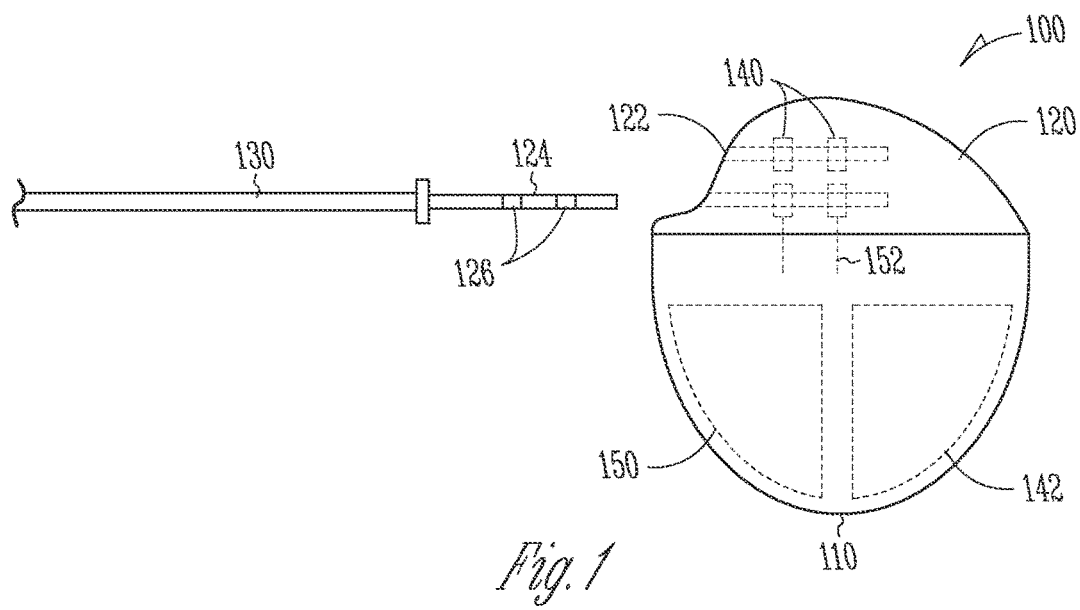
Fig. 1
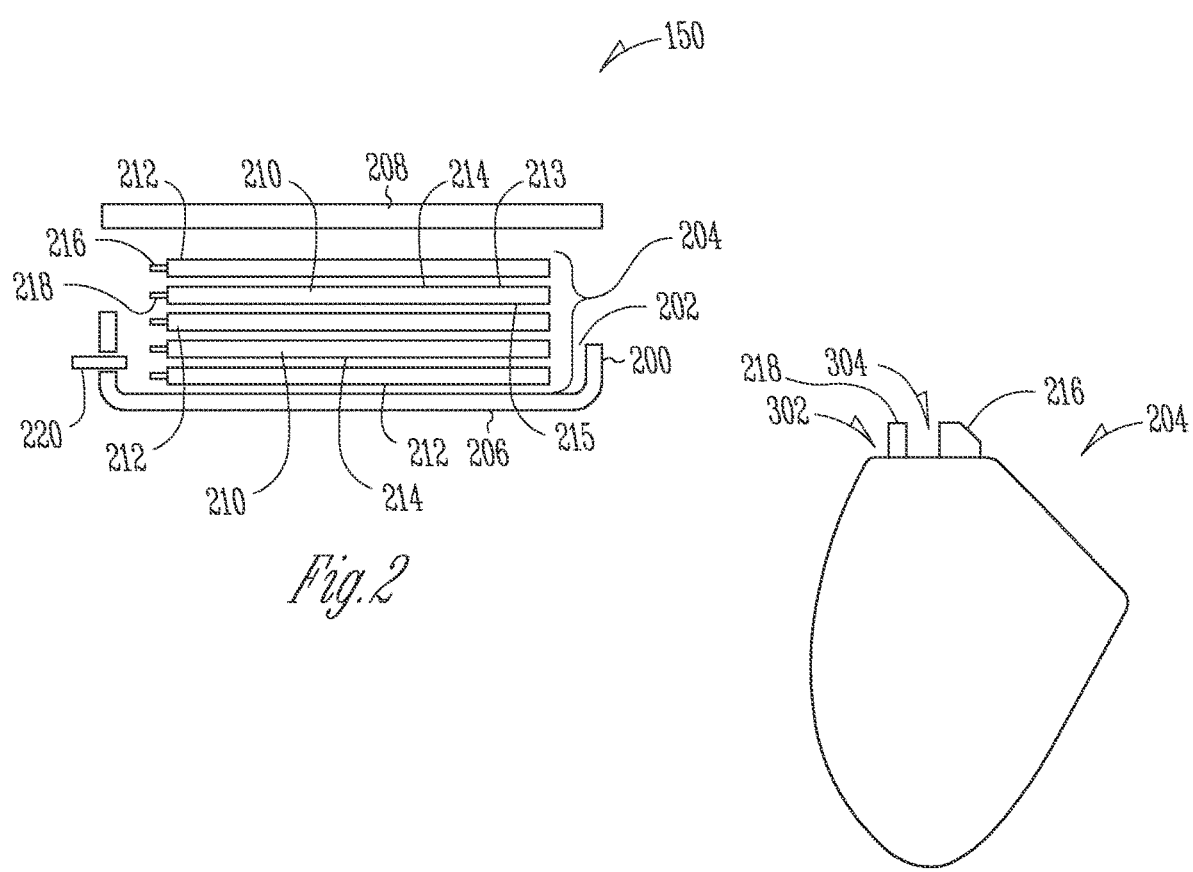
Fig. 2
Fig. 3

BATTERY LITHIUM CLUSTER GROWTH CONTROL

CLAIM OF PRIORITY

This application is a continuation of U.S. application Ser. No. 16/847,823, filed Apr. 14, 2020, which is a continuation of U.S. application Ser. No. 15/583,660, filed May 1, 2017, now issued as U.S. Pat. Ser. No. 10/665,845, which claims the benefit of priority under 35 U.S.C. § 119(e) of U.S. Provisional Patent Application Ser. No. 62/330,317, filed on May 2, 2016, all of which are herein incorporated by reference in their entireties.

BACKGROUND

Implantable devices such as pacemakers or defibrillators include a housing holding electronics including batteries. The long-term reliability of batteries is a concern.

OVERVIEW

Example 1 can include an apparatus including a battery stack including a plurality of alternating anodes and cathodes; wherein each of the anodes is positioned between first and second separators, and wherein a tab of the anode extends out from between the first and second separators; and an edge tape extending across a top of the first and second separators.

In Example 2, the apparatus of Example 1 can optionally include wherein the edge tape covers over a portion of the tab.

In Example 3, the apparatus of any of Examples 1-2 can optionally include wherein the edge tape includes a first tape strip on a first side of the first separator and a second tape strip on an opposite side of the second separator.

In Example 4, the apparatus of any of Examples 1-3 can optionally include a battery case, wherein the battery stack is enclosed within the battery case.

In Example 5, the apparatus of any of Examples 1-4 can optionally include a case tape located on an inner surface of the case proximate a feedthrough, wherein the tape at least partially covers the bottom surface of the case and extends to at least partially cover two sidewalls of the case.

In Example 6, the apparatus of any of Examples 1-5 can optionally include wherein the battery stack is enclosed within a soaker pad enclosure.

In Example 7, the apparatus of any of Examples 1-6 can optionally include wherein the cathodes are enclosed in separator bags.

In Example 8, the apparatus of any of Examples 1-7 can optionally include wherein the edge tape includes a polyamide tape.

In Example 9, the apparatus of any of Examples 1-8 can optionally include wherein the edge tape includes a tape strip having a first portion and a second portion higher than the first portion, wherein the second, higher portion is located over the anode tab.

In Example 10, the apparatus of any of Examples 1-9 can optionally include wherein the battery stack includes lithium anodes with a layer of lithium located on a collector and wherein the edge tape is approximately as thick as the layer of lithium.

In Example 11 an apparatus can include an implantable housing holding electronics; a battery located within the implantable housing, the battery including a battery case and a battery stack within the case, the battery stack including a plurality of alternating anodes and cathodes, wherein each anode is positioned between first and second separators, and wherein a tab of the anode extends out from between the first and second separators; an edge tape extending across a top of the first and second separators; and a case tape located on an inner surface of the battery case proximate a feedthrough, wherein the case tape at least partially covers a bottom surface of the case and extends at least partially up two sidewalls of the case.

In Example 12 the apparatus of Example 11 can optionally include wherein the edge tape covers over a portion of the tab.

In Example 13, the apparatus of any of Examples 11-12 can optionally include wherein the edge tape includes a first tape strip on a first side of the first separator and a second tape strip on an opposite side of the second separator.

In Example 14, the apparatus of any of Examples 11-13 can optionally include wherein the battery stack is enclosed within a soaker pad enclosure.

In Example 15, the apparatus of any of Examples 11-14 can optionally include wherein the cathodes are enclosed in separator bags.

In Example 16, the apparatus of any of Examples 11-15 can optionally include wherein the edge tape includes a tape strip having a first portion and a second portion higher than the first portion, wherein the second, higher portion is located over the anode tab.

In Example 17, the apparatus of any of Examples 11-16 can optionally include wherein the battery stack includes lithium anodes with a layer of lithium located on a collector and wherein the edge tape is approximately as thick as the layer of lithium.

In Example 18 a method can include stacking a plurality of alternating anodes and cathodes into a battery stack, wherein each anode is positioned between first and second separators, and wherein a tab of the anode extends out from between the first and second separators; and placing an edge tape extending across a top of the first and second separators.

In Example 19, the method of Example 18 can optionally include wherein the anode is a lithium anode with lithium located on a collector, and wherein the edge tape is positioned such that it cover a top edge of the collector but does not cover the lithium.

In Example 20, the method of any of Examples 18-19 can optionally include providing a battery case; positioning a case tape on an inner surface of the battery case proximate a feedthrough, wherein the case tape at least partially covers a bottom surface of the case and extends at least partially up two sidewalls of the case; and placing the battery stack into the battery case.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 1 shows an implantable medical device in accordance with one example.

FIG. 2 shows an exploded view of a battery, in accordance with one embodiment.

FIG. 3 shows a top view of the battery stack of FIG. 2.

DETAILED DESCRIPTION

Figure 4:
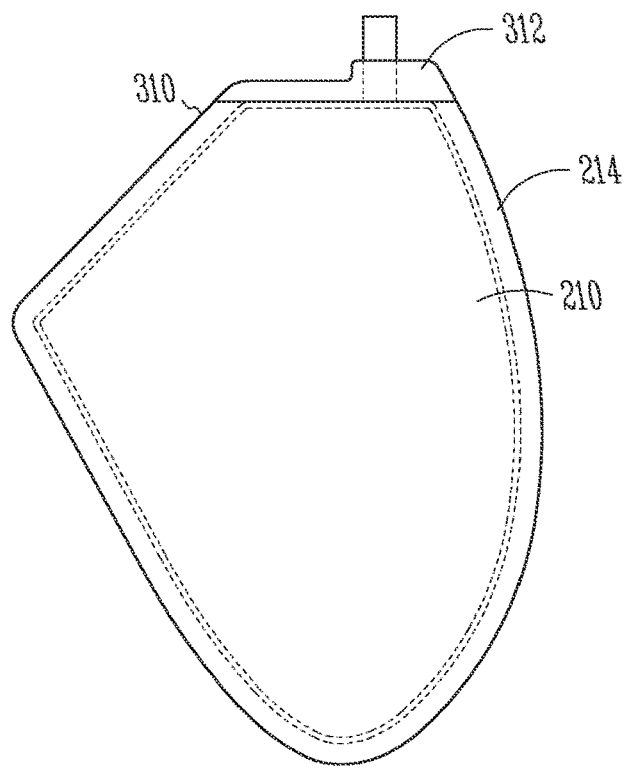
FIG. 4 shows a top view of an anode in accordance with one example.

FIG. 1 shows an implantable medical device 100 in accordance with one example. The implantable medical device 100 includes a metallic housing 110 and an attached header 120. The header 120 includes one or more ports 122 to receive a terminal pin 124 of an implantable lead 130. The lead 130 is configured to deliver pacing pulses, defibrillation shock energy, or cardioversion therapy to a heart, for example. The implantable medical device 100 can be implanted in a surgically-formed pocket in a patient's chest or other desired location.

The implantable medical device 100 generally includes electronic components 142 to perform signal analysis, processing, and control. The implantable medical device 100 can include a power supply such as a battery 150, or a capacitor, and other components housed within housing 110. The implantable medical device 100 can include microprocessors to provide processing and evaluation to determine and deliver electrical shocks and pulses of different energy levels and timing for ventricular defibrillation, cardioversion, and pacing to a heart in response to cardiac arrhythmia including fibrillation, tachycardia, and bradycardia via one or more electrodes of the lead 130.

This device 100 includes one or more connector blocks 140 that connect to feedthroughs 152 to electrically communicate between the header 120 and the electronics 142 and battery 150 within housing 100. Terminal contacts 126 on terminal 124 contact the connector blocks 140 to electrically communicate with electrodes on the lead 130.

In other examples, the battery packaging subject matter discussed below can be used for other battery-powered device, such as sensors.

FIG. 2 shows an exploded view of the battery 150, in accordance with one embodiment.

The battery 150 can include a metallic case 200 defining a chamber 202 which holds a battery stack 204. In one embodiment, the case 200 can be manufactured from a conductive material, such as stainless steel. The case 20 can include a base 206 and a lid 208 positionable on an upper rim of base 206.

The battery stack 204 can include including a plurality of alternating anodes 210 and cathodes 212. Each of the anodes 212 can be positioned between first and second separators 213, 215, with a tab 218 of the anode 212 extending out from between the first and second separators 213, 215. In an example, the first and second separators 213, 215 can be sealed to form a separator bag 214.

Each cathode 212 can include a cathode tab 216 and each anode 210 can include the anode tab 218. As noted, the anode tabs 218 can extend out of the separator bag 214. An electrolyte is placed in the case 200.

After assembly the cathode tabs 216 are electrically connected to each and the anode tabs 218 are electrically connected to each other. A feedthrough post 220 can pass through the case 200 to stack 204 and is electrically insulated from case 200. The feedthrough post 220 can be connected to the cathode tabs 216, while the anode tabs 218 can be directly attached to the case 200, which can itself act as the anode terminal. In some embodiments, these roles are reversed and the cathode tab can be connected to the case and the anode tab can connect to a feedthrough. In some embodiments, two feedthroughs can be provided, one for the anode and one for the cathode, FIG. 3 shows a top view of the battery stack 204. In one example, the anodes 210 can be formed of a lithium layer on a collector, such as a nickel collector. The cathodes 212 can be formed of a cathode material, such as $MnO_2$, coated to a stainless steel wire-mesh collector.

One problem with lithium batteries is minimizing lithium cluster growth in the battery. The lithium cluster growth can initiate where electrolyte pooling is in contact with the anodic surface. In some examples, the pooling and cluster growth can form anywhere within the separator/anode assembly. For example, two areas of lithium cluster growth problems are in the area 302 where the anode tabs 218 come together where a lithium growth can be formed. Also, sometimes an anodic cluster can burst through the separator at an area 304 near the cathode tabs 216 and contact the cathode tab 216, causing a short circuit.

The present discussion includes various packaging methods to prevent and minimize lithium cluster growths in the battery stack 204.

Figure 5:
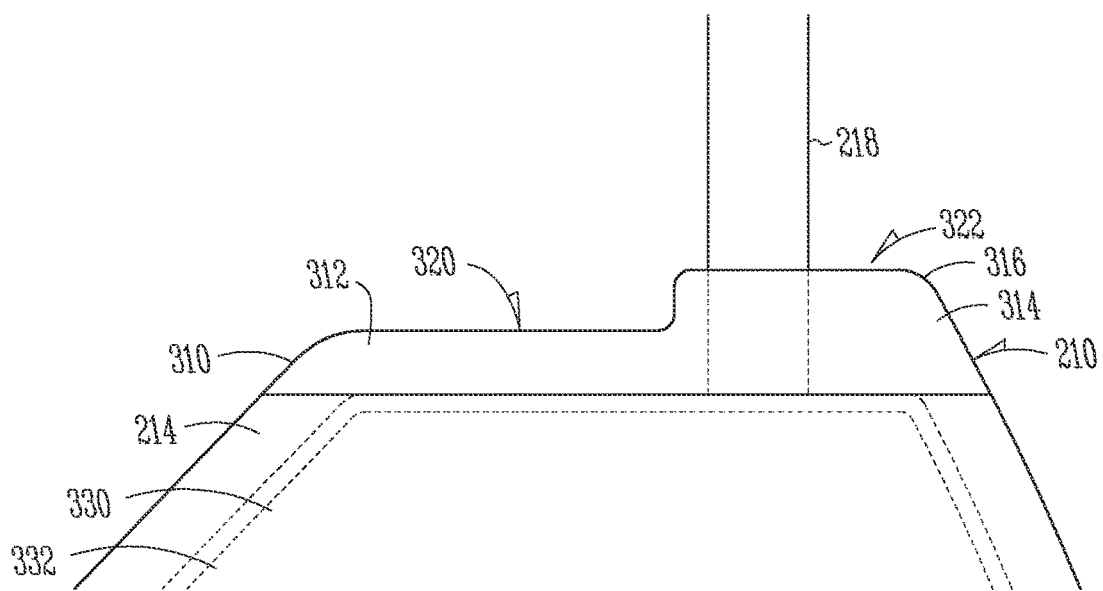
FIG. 5 shows a close-up view of the anode of FIG. 4.

FIG. 4 shows a top view of the anode 218, in accordance with one example; and FIG. 5 shows a close-up view of an upper portion of the anode 210.

As discussed, each anode 210 can be positioned between first and second separators which can be sealed to form a sealed separator bag 214. Various embodiments include separator bags 214 made of a pair of separator layers. The bag is formed around the anode 210 by providing two layers of the separator layers and forming an edge weld seal around the perimeter of the separator layers, forming the separator bag 214. Other separator layers, including additional materials, are within the scope of the present subject matter. An unwelded portion of the separator bag 214 allows tab 218 to extend therethrough.

A problem can arise when electrolyte pools along the upper portion of the anode 210 between the anode 210 and the sealed edge 310 of the separator bag 214. In one embodiment, an edge tape 312 is positioned extending across a top of the first and second separators of separator bag 214 and the top of anode 210. The edge tape 312 can include a first tape strip 311 on a first side of the first separator of separator bag 214 and a second tape strip 316 on an opposite, second side of the second separator of the separator bag 214. The pair of tape strips 314, 316 are mirror images of each other. In an example, the edge tape 312 can include a polyamide tape, or other suitable tape. In one example, the edge tape 312 can be approximately as thick as the thickness of the layer of lithium of the anode. In another example, a single edge tape 312 is used that can wrap around the anode 210 and extend across a top of the first and second separators of separator bag 214 and the top of anode 210.

By extending the edge tape 312 across the entire top portion of the separator bag 214, pooling of electrolyte inside the separator bag 214 along the top edge of the anode 218 can be minimized, thus reducing cluster growth.

The edge tape 312 can include a first portion 320 and a second portion 322 that is higher than the first portion 320. The second, higher portion 322 is located over the anode tab 218. In one example, the edge tape 312 can be positioned such that it covers a top edge of a collector 330 but does not cover a lithium layer 332.

Figure 6:
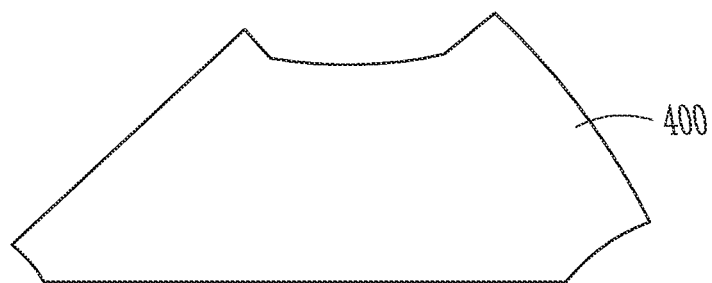
FIG. 6 shows a case tape, in accordance with one embodiment.
Figure 7:
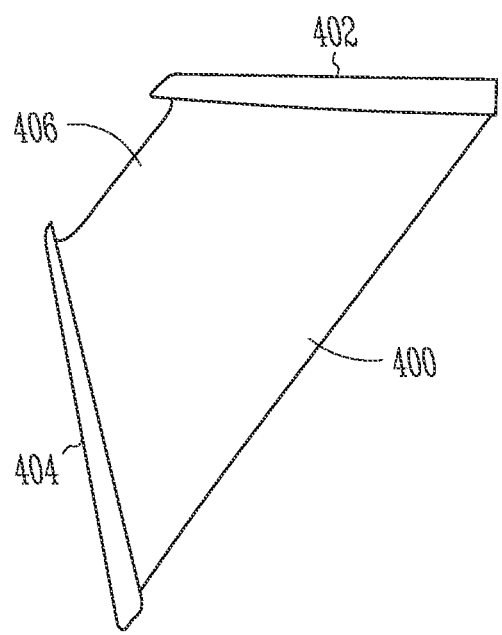
FIG. 7 shows another view of the case tape of FIG. 6.
Figure 8:
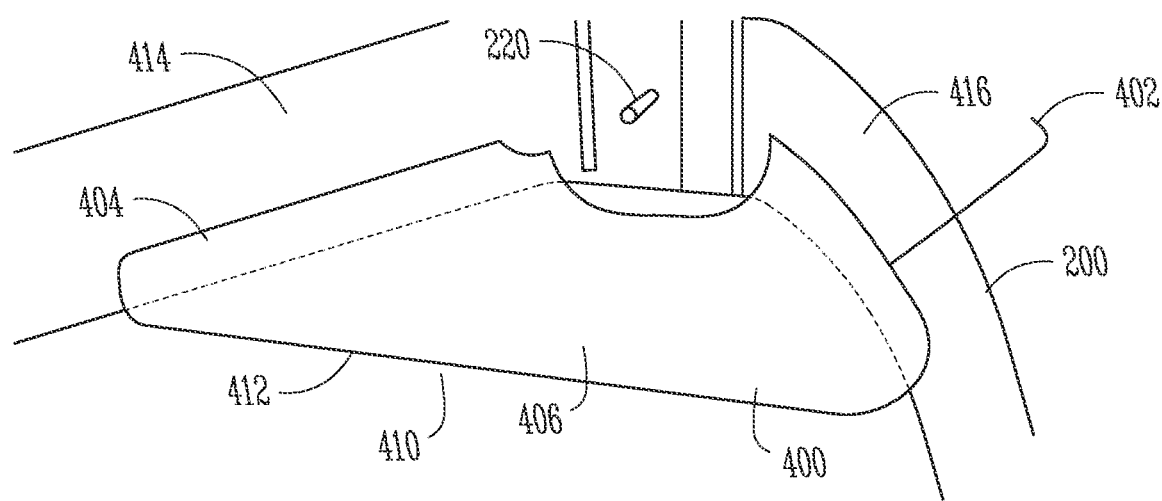
FIG. 8 shows a perspective view of the case tape within a battery case, in accordance with one embodiment.

Another technique to minimize results of lithium cluster growth includes providing a case tape. FIG. 6 shows a case tape 400, in accordance with one embodiment. FIG. 7 shows another view of the case tape 400 folded for insertion into the case; and FIG. 8 shows a perspective view of the case tape 400 within the battery case 200.

The case tape 400 can include a generally irregular shape and can be modified depending on the shape of the battery case. Here, when folded, the case tape 400 has two edges 402 and 404 that curve upward relative to a main portion 406 of the case tape. When the case tape 400 is placed within the case the case tape 400 is positioned and located on an inner surface 410 of the case proximate the feedthrough 220, and the case tape 400 at least partially covers the bottom surface 412 of the case 200 and extends to at least partially cover two sidewalls 414 and 416 of the case 200. In one example, the open side wall area proximate the feedthrough 220 can further be covered with a medical adhesive to seal the anodic battery case surface where the case tape 400 does not cover.

This enlarged case tape 400 prevents any electrolyte pooling from touching the anodic surface, thus minimizing lithium clusters from forming.

Figure 9:
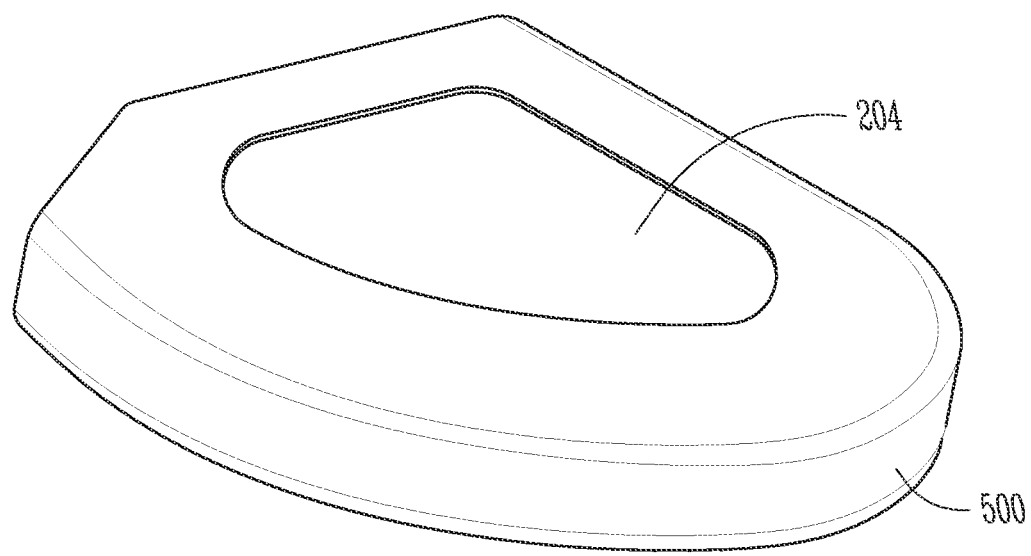
FIG. 9 shows a perspective view of a battery stack within a soaker pad in accordance with one embodiment.
Figure 10:
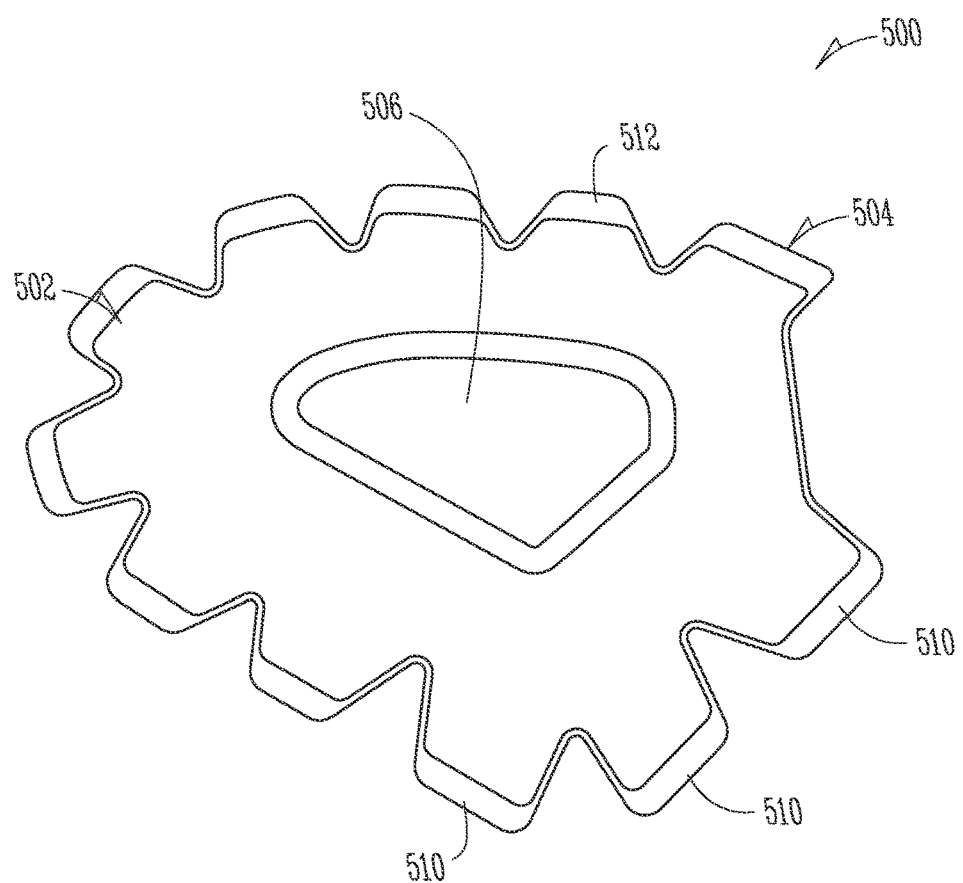
FIG. 10 shows a perspective view of the unfolded soaker tape of FIG. 9.

FIG. 9 shows a perspective view of the battery stack 204 within a soaker pad assembly 500 in accordance with one embodiment. FIG. 10 shows a perspective view of the unfolded soaker pad assembly 500.

The soaker pad assembly 500 includes an internal soaker pad 502, which can be formed of CELGARD, or other suitable material, and an external tape 504, which can be formed of polyamide tape or other suitable tape. The assembly 500 can be designed to be wrapped around the battery stack 204 so that the soaker pad 502 is adjacent the edges of the stack 204. A middle hole 506 can be cut-out of the soaker pad assembly to improve electrolyte wetting of the battery stack. A plurality of fingers 510 are formed in each of the tape 504 and the soaker pad 502 to provide the proper shape when the assembly 500 is wrapped around the stack 204.

The soaker pad assembly 500 is designed to soak or wick up electrolyte from the anode separator bag perimeter. This can help prevent lithium growth clusters. Moreover, by displacing electrolyte away from the anode perimeter, the soaker bag assembly 500 allows for more electrolyte to be housed around the cathodes. This allows the battery to have access to more electrolyte later in the battery's life cycle.

Figure 11:
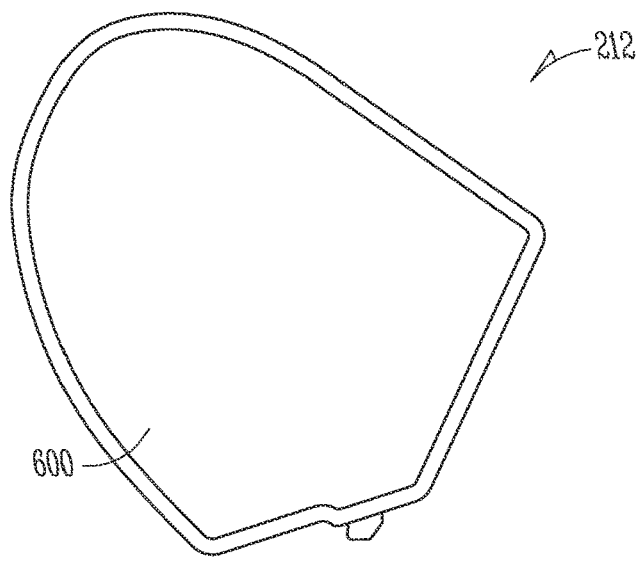
FIG. 11 shows a top view of a cathode enclosed with a bag, in accordance with one embodiment.

FIG. 11 shows a top view of the cathode 212 enclosed within a bag 600, in accordance with one embodiment.

In this example, the cathode is also enclosed within a separator bag with the tab extending out of the bag 600. By using bag 600, the electrolyte from the anode can be better held by the cathode to prevent pooling and to help prevent lithium cluster growth.

In forming a battery using one or more of these techniques described above, a battery stack is formed by stacking a plurality of alternating anodes and cathodes into a battery stack. In an example, each anode is enclosed in a separator bag, with a tab of the anode extends out of the separator bag. An edge tape is positioned so as to extend across a top of the separator bag. The edge tape can be positioned such that the edge tape covers a top edge of the anode collector but does not cover the lithium portion.

Another optional technique is to position a case tape on an inner surface of the battery case proximate the feedthrough. The case tape is sized and positioned such that the case tape at least partially covers a bottom surface of the case and extends at least partially up two sidewalls of the case.

Another optional technique is placing the battery stack into a soaker bag assembly prior to inserting the stack into the battery case. Optionally, the cathode can also be bagged.

In various embodiments, any one or all 4 or any combination of these techniques can be used to help minimize lithium cluster growth.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." in this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The claimed invention is:
1. An apparatus comprising:
a battery stack including a plurality of alternating anodes and cathodes;

wherein each of the anodes is positioned between first and second separators, and wherein a tab of the anode extends out from between the first and second separators; and wherein the battery stack is positioned within a soaker pad assembly.

2. The apparatus of claim 1, wherein the soaker pad assembly includes an internal soaker pad and an external tape.

3. The apparatus of claim 2, wherein the internal soaker pad is positioned adjacent to one or more edges of the battery stack.

4. The apparatus of claim 3, wherein the internal soaker pad is configured to soak up any electrolyte from a perimeter of the anodes.

5. The apparatus of claim 2, wherein the external tape includes a polyamide tape.

6. The apparatus of claim 1, wherein the soaker pad assembly includes a middle hole cut-out of the soaker pad assembly configured to improve electrolyte wetting of the battery stack.

7. The apparatus of claim 1, further including a battery case, wherein the battery stack is enclosed within the battery case.

8. The apparatus of claim 7, including a case tape located on an inner surface of the case proximate a feedthrough, wherein the case tape at least partially covers a bottom surface of the case and extends to at least partially cover two sidewalls of the case.

9. The apparatus of claim 1, further including an edge tape extending across a top of the first and second separators.

10. The apparatus of claim 9, wherein the edge tape covers over a portion of the tab.

11. An apparatus comprising:
an implantable housing holding electronics;
a battery located within the implantable housing, the battery including a battery case and a battery stack within the case, the battery stack including a plurality of alternating anodes and cathodes, wherein each anode is positioned between first and second separators, and wherein a tab of the anode extends out from between the first and second separators;

wherein the battery stack is positioned within a soaker pad assembly.

12. The apparatus of claim 11, wherein the soaker pad assembly includes an internal soaker pad and an external tape.

13. The apparatus of claim 12, wherein the internal soaker pad is positioned adjacent to one or more edges of the battery stack.

14. The apparatus of claim 13, wherein the internal soaker pad is configured to soak up any electrolyte from a perimeter of the anodes.

15. The apparatus of claim 12, wherein the external tape includes a polyamide tape.

16. The apparatus of claim 11, wherein the soaker pad assembly includes a middle hole cut-out of the soaker pad assembly configured to improve electrolyte wetting of the battery stack.

17. The apparatus of claim 11, further including an edge tape extending across a top of the first and second separators.

18. A method comprising:
stacking a plurality of alternating anodes and cathodes into a battery stack, wherein each anode is positioned between first and second separators, and wherein a tab of the anode extends out from between the first and second separators; and positioning a soaker pad assembly around the battery stack.

19. The method of claim 18, wherein the soaker pad assembly includes an internal soaker pad and an external tape.

20. The method of claim 19, wherein the internal soaker pad is positioned adjacent to one or more edges of the battery stack and is configured to soak up any electrolyte from a perimeter of the anodes.

* * * * *